(12) United States Patent
Adler, Jr. et al.

(10) Patent No.: US 10,449,393 B2
(45) Date of Patent: Oct. 22, 2019

(54) RADIATION SYSTEMS WITH MINIMAL OR NO SHIELDING REQUIREMENT ON BUILDING

(71) Applicant: VARIAN MEDICAL SYSTEMS, INC., Palo Alto, CA (US)

(72) Inventors: John R. Adler, Jr., Stanford, CA (US); David H. Whittum, Sunnyvale, CA (US); Steven W. Prince, San Francisco, CA (US); James E. Clayton, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 618 days.

(21) Appl. No.: 15/095,927

(22) Filed: Apr. 11, 2016

(65) Prior Publication Data

US 2016/0220848 A1 Aug. 4, 2016

Related U.S. Application Data

(63) Continuation of application No. 13/310,582, filed on Dec. 2, 2011, now Pat. No. 9,308,395.

(51) Int. Cl.
*A61N 5/10* (2006.01)
*G21F 5/02* (2006.01)
(Continued)

(52) U.S. Cl.
CPC .......... *A61N 5/1081* (2013.01); *A61N 5/1082* (2013.01); *G21F 5/02* (2013.01);
(Continued)

(58) Field of Classification Search
CPC .......... A61N 5/1081; A61N 2005/1094; A61N 2005/1095; A61N 5/1082; A61B 6/107; G21F 3/00; G21F 5/02; G21F 7/00
See application file for complete search history.

(56) References Cited

U.S. PATENT DOCUMENTS

| 3,082,322 A | 3/1963 | Koerner et al. |
|---|---|---|
| 3,488,495 A | 1/1970 | Schneeman |

(Continued)

FOREIGN PATENT DOCUMENTS

| CN | 2533895 Y | 2/2003 |
|---|---|---|
| CN | 101312691 A | 11/2008 |

(Continued)

OTHER PUBLICATIONS

International Search Report and Written Opinion dated Feb. 5, 2013, for related PCT Patent Application No. PCT/US2012/067453.

(Continued)

*Primary Examiner* — Chih-Cheng Kao
(74) *Attorney, Agent, or Firm* — Vista IP Law Group, LLP

(57) ABSTRACT

A radiation system includes a support, a capsule rotatably coupled to the support, a radiation source movably coupled to the capsule, wherein the radiation source is configured to provide a treatment radiation beam, and is capable of being turned on or off in response to a control signal, and a collimator located next to the radiation source, wherein the capsule defines a space for accommodating a portion of a patient, and includes a shielding material for attenuating radiation resulted from an operation of the radiation source, and wherein the shielding material is configured to limit a radiation exposure level to 5 mR/hr or less within 5 meters from an isocenter.

12 Claims, 11 Drawing Sheets

(51) Int. Cl.
- *A61B 6/10* (2006.01)
- *G21F 3/00* (2006.01)
- *G21F 7/00* (2006.01)

(52) U.S. Cl.
CPC ....... *A61B 6/107* (2013.01); *A61N 2005/1094* (2013.01); *A61N 2005/1095* (2013.01); *G21F 3/00* (2013.01); *G21F 7/00* (2013.01)

(56) References Cited

U.S. PATENT DOCUMENTS

| | | | |
|---|---|---|---|
| 3,588,499 | A | 6/1971 | Pegrum |
| 4,977,585 | A | 12/1990 | Boyd |
| 5,420,427 | A | 5/1995 | Morgan et al. |
| 5,537,452 | A | 7/1996 | Shepherd et al. |
| 5,751,781 | A | 5/1998 | Brown et al. |
| 5,993,373 | A | 11/1999 | Nonaka |
| 6,104,779 | A | 8/2000 | Shepherd et al. |
| 6,198,957 | B1 | 3/2001 | Green |
| 6,217,214 | B1 * | 4/2001 | Cabral .................. A61B 6/0421 378/196 |
| 6,325,538 | B1 | 12/2001 | Heesch |
| 6,888,919 | B2 | 5/2005 | Graf |
| 6,977,987 | B2 | 12/2005 | Yamashita |
| 7,188,999 | B2 | 3/2007 | Mihara |
| 7,295,648 | B2 | 11/2007 | Brown |
| 7,302,038 | B2 | 11/2007 | Mackie et al. |
| 7,526,066 | B2 | 4/2009 | Koshnitsky et al. |
| 7,649,981 | B2 | 1/2010 | Seppi et al. |
| 8,664,618 | B2 | 3/2014 | Yao |
| 9,308,395 | B2 | 4/2016 | Adler, Jr. et al. |
| 2002/0150207 | A1 * | 10/2002 | Kapatoes ............. A61N 5/1042 378/65 |
| 2003/0086526 | A1 * | 5/2003 | Clark .................. A61N 5/1049 378/64 |
| 2005/0197564 | A1 | 9/2005 | Dempsey |
| 2005/0236588 | A1 | 10/2005 | Ein-Gal |
| 2009/0110146 | A1 * | 4/2009 | Sliski ...................... A61N 5/10 378/65 |
| 2010/0002829 | A1 | 1/2010 | Dafni |
| 2010/0239066 | A1 | 9/2010 | Fahrig et al. |
| 2011/0210261 | A1 * | 9/2011 | Maurer, Jr. ............. A61N 5/10 250/393 |

FOREIGN PATENT DOCUMENTS

| | | |
|---|---|---|
| CN | 101496727 A | 8/2009 |
| FR | 1 587 608 A | 3/1970 |

OTHER PUBLICATIONS

First Chinese Office Action and Search Report dated Dec. 28, 2015, for related Chinese Patent Application No. 201280068583.0, 13 pages.
Extended European Search Report dated Dec. 23, 2014 for related EP Patent Application No. 12854268.5, 9 pages.
Non-final Office Action dated Jan. 24, 2014 for related U.S. Appl. No. 13/310,582.
Final Office Action dated Aug. 27, 2014 for related U.S. Appl. No. 13/310,582.
Advisory Action dated Nov. 21, 2014 for related U.S. Appl. No. 13/310,582.
Non-final Office Action dated Apr. 6, 2015 for related U.S. Appl. No. 13/310,582.
Final Office Action dated Sep. 11, 2015 for related U.S. Appl. No. 13/310,582.
Notice of Allowance and Fee(s) due dated Dec. 4, 2015 for related U.S. Appl. No. 13/310,582.
Final Office Action dated Dec. 30, 2016, for related U.S. Appl. No. 14/017,992.
Definition of Capsule from dictionary.com printed from Internet Dec. 26, 2016.
Notice of Allowance—Notification of Grant dated Dec. 1, 2016, for corresponding Chinese Patent Application No. 201280068583.0, 2 pages.
Intention to Grant dated Aug. 3, 2017 for related/corresponding European Patent Application No. 12854268.5, 66 pages.
Notice of Allowance and Fee(s) due dated May 4, 2017 for related U.S. Appl. No. 14/017,992.
Communication pursuant to Article 94(3) EPC dated Sep. 20, 2016, for corresponding European Patent Application No. 12 854 268.5, 4 pages.
Notification of Second Office Action dated Aug. 25, 2016 for corresponding Chinese Patent Application No. 201280068583.0, 6 pages.
Non-final Office Action dated Jun. 17, 2016 for related U.S. Appl. No. 14/017,992.
First Chinese Office Action and Search Report dated Jan. 2, 2019 for related Chinese Patent Application No. 2017100844653, 15 pages.
Second Chinese Office Action dated Jul. 9, 2019 for related Chinese Patent Application No. 2017100844653.

* cited by examiner

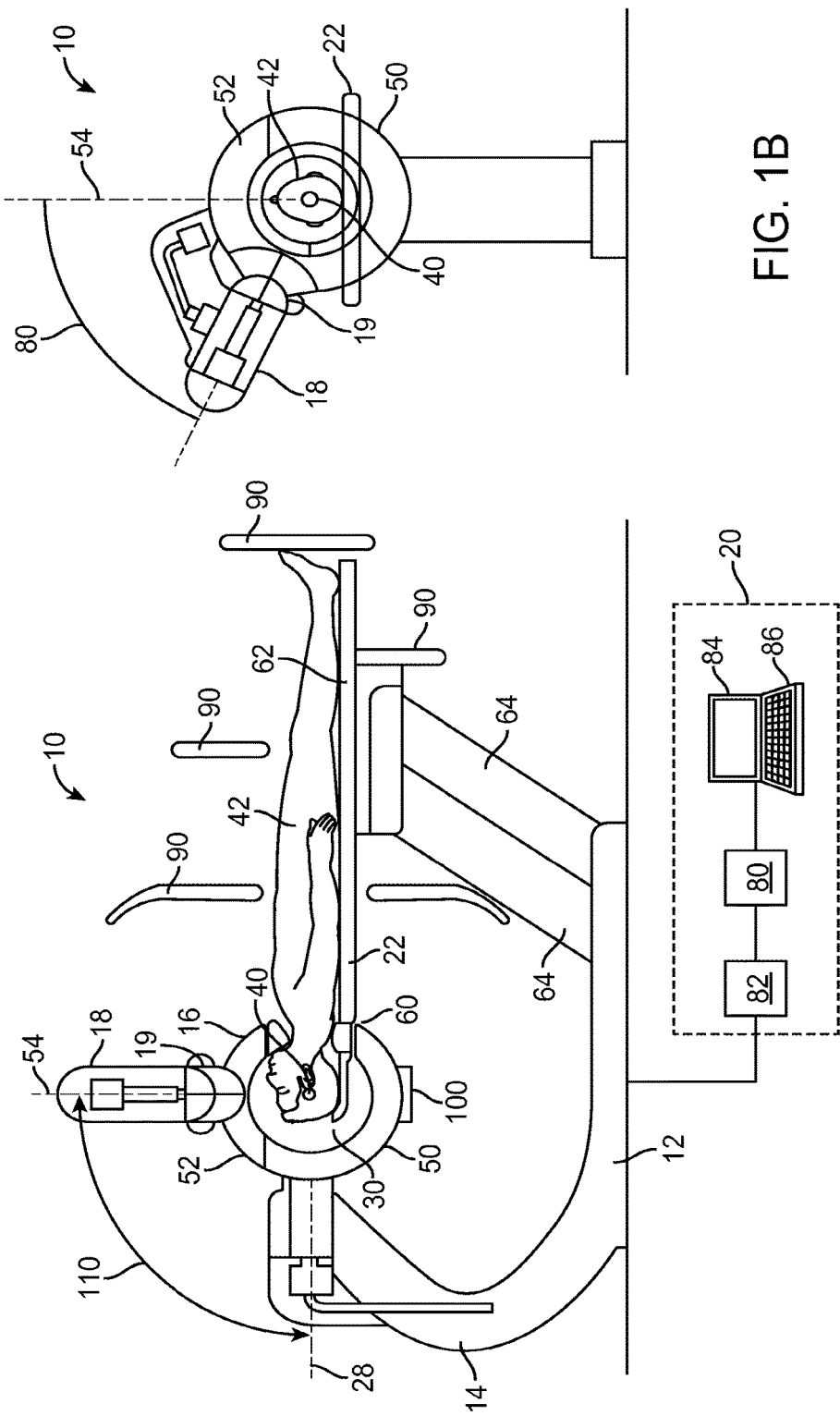

RADIATION SYSTEMS WITH MINIMAL OR NO SHIELDING REQUIREMENT ON BUILDING

RELATED APPLICATION DATA

This application is a continuation of U.S. patent application Ser. No. 13/310,582, filed Dec. 2, 2011, pending. The entire disclosure of the above application is expressly incorporated by reference herein.

FIELD

This application relates generally to radiation systems, and more particularly, to radiation treatment systems.

BACKGROUND

Radiation has been employed for diagnostic purposes. For example, radiation may be used in an x-ray procedure or a CT procedure to obtain images of a patient. Radiation has also been employed to treat tumorous tissue. In radiation therapy, a high energy beam is applied from an external source towards the patient. The radiation source, which may be rotating (as in the case for arc therapy), produces a collimated beam of radiation that is directed into the patient to the target site. Sometimes, in radiation therapy, the high energy radiation may also be used for imaging the patient.

Existing radiation systems for imaging and/or treatment generate a significant amount of radiation during a procedure. Thus, in existing facilities that provide radiation machines, the building structures housing the radiation machines are required to be retrofitted to provide adequate radiation shielding. This ensures that radiation generated by radiation machine does not cause harm to the operator of the radiation machine, or to other occupants of the building who are not the intended recipient of the radiation.

Applicant of the subject application determines that new radiation systems would be desirable.

SUMMARY

In accordance with some embodiments, a radiation system includes a support, a capsule rotatably coupled to the support, a radiation source movably coupled to the capsule, wherein the radiation source is configured to provide a treatment radiation beam, and is capable of being turned on or off in response to a control signal, and a collimator located next to the radiation source, wherein the capsule defines a space for accommodating a portion of a patient, and includes a shielding material for attenuating radiation resulted from an operation of the radiation source, and wherein the shielding material is configured to limit a radiation exposure level to 5 mR/hr or less within 3 meters from an isocenter.

In accordance with other embodiments, a radiation system includes a patient support configured to support a patient in an upright position, wherein the patient support is rotatable about a vertical axis, a gantry defining a space for accommodating at least a portion of the patient, and a radiation source mounted on the gantry, wherein the gantry is configured to translate in a vertical direction to move the radiation source vertically.

In accordance with other embodiments, a radiation method includes delivering radiation beam from a radiation source towards a portion of a patient, and rotating the patient relative to the radiation source, wherein the patient is rotated while the radiation beam is being delivered to the portion of the patient.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 1A illustrates a radiation system in accordance with some embodiments;

FIG. 1B illustrates an end view of the radiation system of FIG. 1A in accordance with some embodiments;

DESCRIPTION OF THE EMBODIMENTS

Figure 2A:
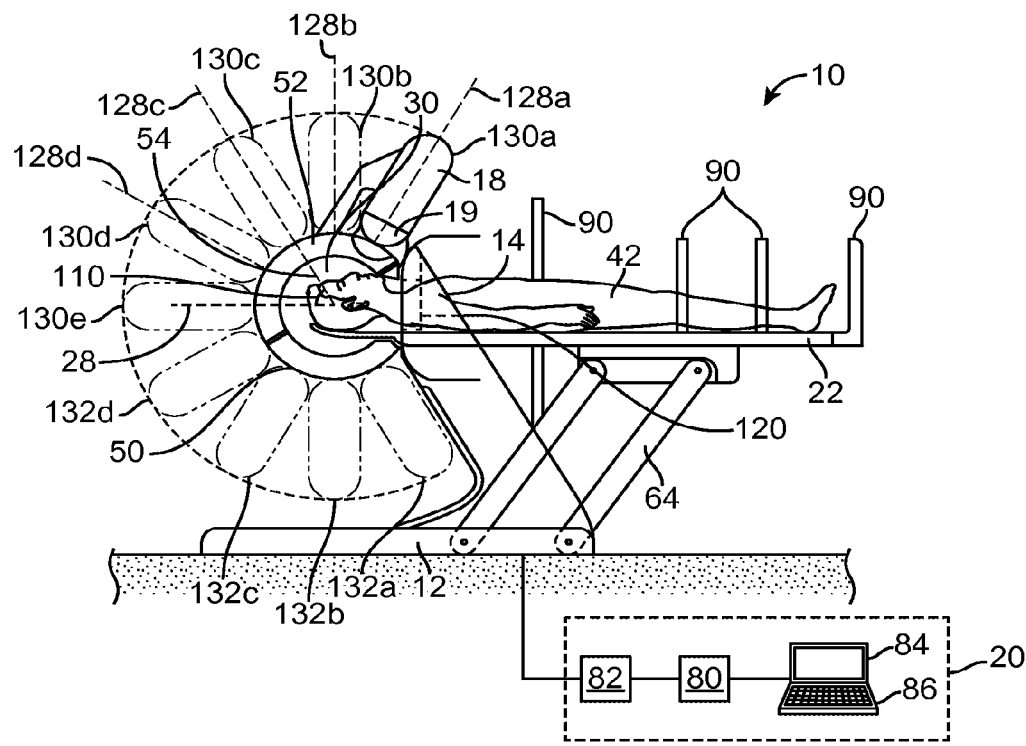
FIG. 2A illustrates another radiation system in accordance with other embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1A illustrates a radiation system 10 in accordance with some embodiments. The radiation system 10 includes a base 12, a support 14, a capsule 16, a radiation source 18, a collimator 19, a control system 20, and a patient support 22. In the illustrated embodiments, the base 12 and the support 14 are manufactured as a single piece with an unity configuration. In other embodiments, the base 12 and the support 14 may be separate components that are coupled together. Also, in further embodiments, the support 14 may be moveable relative to the base 12 in one or more degrees of freedom. In still further embodiments, the base 12 may be considered to be a part of the support 14.

In the illustrated embodiments, the capsule 16 is rotatably coupled to the support 14 about axis 28, and defines a space 30 for accommodating at least a portion 40 of a patient 42. As used in this specification, the term "capsule" may refer to any structure (which may be a single component, or a plurality of components) that at least partially defines a space for accommodating an object, such as a portion of the patient 42, and should not be limited to structures that provide full enclosure, or structures having any particular shapes. In the illustrated embodiments, the portion 40 is a head of the patient 42. In other embodiments, the portion 40 may include other part(s) of the patient 42. For example, in other embodiments, the portion 40 may include both the head and the shoulders of the patient 42. In further embodiments, the portion 40 may include a body of the patient 42.

As shown in the figure, the capsule 16 includes a first capsule portion 50 and a second capsule portion 52 that is rotatable relative to the first capsule portion 50 about axis 54. In one implementation, the first capsule portion 50 and the second capsule portion 52 may be rotatably coupled to each other using a tongue-and-groove mechanism, which may be more effective in preventing leakage of radiation between the coupling of the portions 50, 52 (because part of the tongue-and-groove mechanism may attenuate some of the radiation). In other embodiments, the first and second capsule portions 50, 52 may be coupled using other mechanisms. In the illustrated embodiments, the first and second capsule portions 50, 52 define an interior surface that has a partial spherical configuration. In other embodiments, the interior surface may have other configurations, and is not limited to a spherical configuration.

In the illustrated embodiments, the capsule 16 includes a shielding material that is configured to block at least some of the radiation that is resulted from an operation of the radiation source 18. The shielding material may include any material(s) that is known for providing radiation shielding, including but not limited to steel, lead, tungsten, or combination thereof. In some embodiments, the shielding material may be used to make the wall of the capsule 16. In other embodiments, the shielding material may be coupled to the wall of the capsule 16. For examples, the shielding material may be coupled to an outside surface of the wall of the capsule 16, an inside surface of the wall of the capsule 16, or may be a layer that is embedded within the wall of the capsule 16. In addition, in other embodiments, the shielding material may be in a form of multiple layers that are coupled to the capsule 16, with one or more layers coupled to an outside surface of the wall of the capsule 16, one or more layers embedded in the wall of the capsule 16, one or more layers coupled to an inside surface of the wall of the capsule 16, or combination thereof. Also, in some embodiments, the shielding material may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. For example, the shielding requirement for the entire room may be reduced, or only portion(s) of the room may need to be retrofitted for shielding requirement.

In the illustrated embodiments of FIG. 1A, the radiation source 18 is a treatment radiation source that is configured to provide a treatment radiation beam towards an isocenter that coincides with a target region in the portion 40 of the patient 42. The radiation source 18 may be capable of being turned on or off in response to a control signal (e.g., a signal from a control unit, etc.). Alternatively it may be a radioactive source which is not capable of being turned off, but may be shuttered. The radiation source 18 may be configured to generate a cone beam, a fan beam, or other types of radiation beams in different embodiments. The radiation source 18 may be implemented using a x-band linear accelerator. In other embodiments, the radiation source 18 may be implemented using other types of linear accelerator. It should be noted that as used in this specification, the term "radiation source" or similar terms, such as "source", refers to a component from which a radiation or energy is emitted, and may or may not include an accelerator. Also, in the illustrated embodiments, the radiation source 18 is configured to provide the treatment radiation beam having an energy level that is anywhere from 0.2 MV to 8 MV, and more preferably, anywhere from 0.9 MV to 3 MV. In other embodiments, the radiation source 18 may be configured to provide the treatment radiation beam having other energy levels, such as lower than 0.2 MV or higher than 8 MV. However, providing radiation beam having an energy level that is at or below 3 MV is more desirable because it may obviate the need to add shielding to the building of the facility, or at least reduce some of the shielding requirement for the building. In other embodiments, shielding to a building may also not be required even for radiation beam having an energy level that is higher than 3 MV. Such may be accomplished by configuring the shielding of the system 10 (e.g., providing thicker shielding, and/or using more dense material(s), etc.).

Also, in other embodiments, a small beam tube may be employed in conjunction with closely packed shielding to further reduce radiation exposure. To obtain close proximity to the beam, and further reduce the solid-angle to the target, the shielding may be built into the accelerator structure, employing for example dense conductive materials such as Elkonite. With the aid of electromagnets or permanent magnets, a serpentine beam tube may be employed to block line of sight to the target, and to aid shielding of radiation exposure. An example would involve use of a bend magnet, preferably achromatic.

In the illustrated embodiments, the source to isocenter distance (SID) or source-axis distance (SAD) is less than 800 mm, and more preferably less than 600 mm, and even more preferably around 415 mm (415 mm±40 mm). Also, in some embodiments, the SID/SAD value for the radiation system 10 is less than those in existing radiation machines. Such configuration allows the radiation source 18 to provide less radiation energy compared to existing treatment radiation sources, and still sufficiently treats a target (e.g., tumor, or a nerve). Also, because of the reduction in energy requirement, the amount of shielding that is needed for a facility building is substantially reduced, or may be eliminated. Furthermore, because of the reduction in energy requirement, the size of the accelerator for generating the radiation may be reduced. This in turn reduces the weight of the system 10, thereby obviating any need to retrofit a building, or at least reducing an amount of retrofit required, for supporting a weight of the system 10. In other embodiments, the SID/SAD may have other values.

As shown in FIG. 1B, which is an end view of the system 10 of FIG. 1A, the radiation source 18 is tilted so that it forms an angle 80 (e.g., a non-zero acute angle) relative to the axis 54. Such configuration allows the radiation source 18 to deliver radiation from different angles towards the portion 40 of the patient 42 as the second portion 52 rotates relative to the first portion 50 about the axis 54. In other embodiments, the capsule 16 may be rotated about the axis 28 to turn the radiation source 18 around the patient so that radiation may be delivered to the patient from different angles. In some embodiments, the rotation of the portion 52 about the axis 54, and the rotation of the capsule about the axis 28, may be performed one after the other. Alternatively, the rotation of the portion 52 about the axis 54, and the rotation of the capsule about the axis 28, may be performed simultaneously. In some embodiments, the radiation source 18 may be configured to be tiltable relative to the second portion 52.

Returning to FIG. 1A, the collimator 19 is located next to the radiation source 18, and is configured to shape the radiation beam from the source 18 in accordance with a treatment plan. In some embodiments, the collimator 19 may be considered to be a part of the radiation source 18. As shown in the figure, none of the components from the radiation source 18 or the collimator 19 extends into the space 30. This creates the interior surface of the capsule 16 that maintains a clearance to the portion of the patient inside the space 30, thereby avoiding the risk of having a component that collides with the portion of the patient that is inside the space 30 as the capsule 16 rotates about the axis 28, and/or as the second capsule portion 52 rotates about the axis 54. In other embodiments, instead of a collimator, component 19 may be a cone with an outlet having a pre-defined configuration, an iris that provides an outlet having a cross-section that is adjustable, or any of other devices that is capable of blocking at least some of the radiation provided from the radiation source 18. In one or more embodiments, the component 19 may be configured to block/attenuate at least 98% of the radiation (e.g., within the treatment field), and more preferably at least 99.9% of the radiation (e.g., outside of the treatment field).

As shown in FIG. 1A, the capsule 16 also includes an opening 60 for allowing the portion 40 of the patient 42 to go therethrough in order to reach the interior space 30 of the capsule 16. The patient support 22 includes a table 62 for supporting the patient 42, and a positioner 64 configured to translate the table 62 axially so that the portion 40 of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60 at the capsule 16. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions relative to the capsule 16. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

In the illustrated embodiments, the control system 20 includes a processor 80, such as a computer processor, coupled to a control 82. The control system 20 may also include a monitor 84 for displaying data and an input device 86, such as a keyboard or a mouse, for inputting data. In the illustrated embodiments, during an imaging and/or treatment procedure, the capsule 16 rotates about the patient 42 (as in a CT procedure and/or an arch-therapy). The operation of the radiation source 18 and the capsule 16 are controlled by the control 82, which provides power and timing signals to the radiation source 18 and the collimator system 19, and controls a rotational speed and position of the capsule 16, and/or a rotational speed and position of the portion 52 relative to the portion 50, based on signals received from the processor 80. Although the control 20 is shown as a separate component from the capsule 16 and the processor 80, in alternative embodiments, the control 20 may be a part of the capsule 16 or the processor 80.

In some embodiments, movement of the components of the system 10 (e.g., the capsule 16, the portion 52, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

As shown in FIG. 1A, the radiation system 10 may optionally further include one or more shields 90 for blocking radiation that is resulted from an operation of the radiation source 18. The shield(s) 90 may be coupled to the patient support 22, the support 14, the capsule 16, the radiation source 18, any of other components in the system 10, or any combination thereof. The additional shield(s) 90 is advantageous because it allows the capsule 16 to block less radiation. For example, in some embodiments, the shielding material at the capsule 16 may be configured to block radiation so that it attenuates at least 98%, and more preferably at least 99.9%, and even more preferably at least 99.999%, of the radiation (e.g., photons/charged particles, such as electrons, neutrons, etc.), resulted from an operation of the radiation source 18 traveling therethrough. In some embodiments, the shielding material at the capsule 16, and the additional shield(s) 90, may be configured to block off a sufficient amount of radiation resulted from an operation of the radiation source 18 so that they obviate the need to provide shielding at a facility building, such as at a hospital.

In other embodiments, instead of completely eliminating shielding at a building, the shielding material at the capsule 16, and the additional shield(s) 90, may be configured to block off a sufficient amount of radiation resulted from an operation of the radiation source 18, so that they reduce a significant amount (e.g., at least 50%, and more preferably, at least 90%) of the shielding requirement at a building. In other embodiments, the shield(s) 90 may be configured to block off all or most of the radiation resulted from an operation of the radiation source 18. In such cases, the capsule 16 may not include any shielding material.

It should be noted that the shield(s) 90 is not limited to the configuration shown in the illustrated embodiments, and that in other embodiments, the shield(s) 90 may have different configurations (e.g., shapes). For example, in other embodiments, the shield 90 may be in a form of a tube or container that houses a part (e.g., the body, legs, or both, etc.) of the patient 42.

Also, as shown in FIG. 1A, the radiation system 10 may optionally further include an imager 100 in accordance with some embodiments. The imager (imaging panel) 100 may be based on amorphous silicon or any of other technologies known in the art. The imager 100 is located at an operative position relative to the source 18 (e.g., on the side of the capsule 16 that is opposite from the source 18). During use, radiation from the radiation source 18 enters the patient 42 and exits the patient 42 to reach the imager 100. The imager 100 generates image data in response to the radiation received thereon. The radiation may be treatment radiation in some embodiments, or may be diagnostic radiation in other embodiments. In some embodiments, the image data may be generated before a treatment session using diagnostic radiation to setup the patient 42 (e.g., before treatment radiation is delivered to the patient 42). In other embodiments, the image data may be generated during a treatment session to confirm an accuracy of treatment radiation delivery. In further embodiments, the image data may be processed by the processor 80, which adjusts a treatment plan based on the processed image data. For example, if the processor 80 determines from the image data that a part of a target region is not receiving enough radiation, and/or if a critical (e.g., healthy) tissue is receiving too much radiation, the processor 80 may then adjust the treatment plan so that a future delivery of treatment radiation would result in more radiation being delivered to the target region and/or less radiation being delivered to the critical tissue.

Also, in one or more embodiments described herein, the radiation system 10 may optionally further include one or more imaging sources (e.g., two x-ray sources in keV range) and one or more corresponding imagers that are in corresponding operative positions relative to the imaging source(s). The imager(s) may be coupled to the base 12, to the capsule 16, to the support 22, or to any component of the radiation system 10. In other embodiments, the imager(s) may be coupled to another structure that is not a part of the radiation system 10. For example, in other embodiments, the imager(s) may be mounted to a room (e.g., to a ceiling, a floor), or to a support that is movable independent of the base 12. During use, radiation from the imaging source(s) enters the patient 42 and exits the patient 42 to reach the corresponding imager(s). The imager(s) generates image data in response to the radiation received thereon. In some embodiments, the image data may be generated before a treatment session using diagnostic radiation to setup the patient 42 (e.g., before treatment radiation is delivered to the patient 42). In other embodiments, the image data may be generated during a treatment session to confirm an accuracy of treatment radiation delivery. In further embodiments, the image data may be processed by the processor 80, which adjusts a treatment plan based on the processed image data. For example, if the processor 80 determines from the image data that a part of a target region is not receiving enough radiation, and/or if a critical (e.g., healthy) tissue is receiving too much radiation, the processor 80 may then adjust the treatment plan so that a future delivery of treatment radiation would result in more radiation being delivered to the target region and/or less radiation being delivered to the critical tissue.

It should be noted that the radiation system 10 is not limited to the examples described previously, and that the radiation system 10 may have different configurations in different embodiments.

For example, in other embodiments, instead of being a treatment source, the radiation source 18 may be a diagnostic radiation source for providing diagnostic energy. In such cases, the imager 100 is configured to receive diagnostic radiation (e.g., radiation generated at keV energy level) and generate image signals in response thereto. In other embodiments, in addition to being a treatment radiation source, the radiation source 18 may also be a diagnostic radiation source for providing diagnostic energy. In such cases, the imager 100 is configured to selectively receive diagnostic radiation or treatment radiation and generate image signals in response thereto.

In some embodiments, treatment energy is an energy having a value that is higher than 160 kilo-electron-volts (keV), and more preferably, higher than 0.9 mega-electron-volts (MeV) (e.g., 8 MeV or lower). Also, in some embodiments, diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 18 is able to generate X-ray radiation at a plurality of photon energy levels within a range anywhere from 10 keV to 20 MeV, and more preferably, from 10 keV to 3 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003.

In further embodiments, the structure 16 supporting the radiation source 18 may have different configurations as those described. For example, in other embodiments, the structure 16 may have a ring configuration, as in a ring gantry. In further embodiments, the structure 16 may include an arm for carrying the radiation source 18. The arm may have an L-shape, a C-shape, or any other shapes in different embodiments. If a C-shape arm (C-arm) is used, one end of the arm may carry the radiation source 18, the other end of the arm may carry the imager 100, and the middle segment of the C-arm may be rotatably coupled to a support structure.

In the above embodiments, the axis 54 of rotation for the second portion 52, and the axis 28 of rotation for the first portion 50 form an angle 110 that is approximately 90° (i.e., 90°±10°). In other embodiments, the angle 110 between the axes 28, 54 may be different to provide different angular coverage by the system 10.

FIG. 2A illustrates another radiation system 10 in accordance with other embodiments. The system 10 of FIG. 2A is similar to that of FIG. 1, except that the support 14 is located on the left and right sides of the patient support 22. In particular, the support 14 has a first portion that is next to a left side of the patient support 22, and a second portion that is next to a right side of the patient support 22. The first and second portions of the support 14 are coupled together by a support component 120 that extends between the first and second portions of the support 14. The support component 120 has an opening for allowing a portion of the patient to be inserted therethrough to reach the space 30. The first portion 50 of the capsule 16 is rotatably coupled to the support component 120 so that the first portion 50 may rotate about the axis 28. The second portion 52 of the capsule 16 is rotatably coupled to the first portion 50 so that the second portion 52 may rotate about the axis 54.

During use, the second portion 52 may be selectively rotated about the axis 54 relative to the first portion 50, to place the radiation source 18 at a position that lies in plane 128a. The radiation source 18 may then be rotated around the patient by rotating the first portion 50 about the axis 28 relative to the support component 120, thereby placing the radiation source 18 at different positions around the patient (such as positions 130a, 132a). As the first portion 50 is rotated about the axis 28, treatment radiation or imaging radiation may be delivered to the patient.

In another example, the second portion 52 may be selectively rotated about the axis 54 relative to the first portion 50, to place the radiation source 18 at a position that lies in plane 128b. The radiation source 18 may then be rotated around the patient by rotating the first portion 50 about the axis 28 relative to the support component 120, thereby placing the radiation source 18 at different positions around the patient (such as positions 130b, 132b). As the first portion 50 is rotated about the axis 28, treatment radiation or imaging radiation may be delivered to the patient.

In another example, the second portion 52 may be selectively rotated about the axis 54 relative to the first portion 50, to place the radiation source 18 at a position that lies in plane 128c. The radiation source 18 may then be rotated around the patient by rotating the first portion 50 about the axis 28 relative to the support component 120, thereby placing the radiation source 18 at different positions around the patient (such as positions 130c, 132c). As the first portion 50 is rotated about the axis 28, treatment radiation or imaging radiation may be delivered to the patient.

In still another example, the second portion 52 may be selectively rotated about the axis 54 relative to the first portion 50, to place the radiation source 18 at a position that lies in plane 128d. The radiation source 18 may then be rotated around the patient by rotating the first portion 50 about the axis 28 relative to the support component 120, thereby placing the radiation source 18 at different positions around the patient (such as positions 130d, 132d). As the first portion 50 is rotated about the axis 28, treatment radiation or imaging radiation may be delivered to the patient.

In further embodiments, during use, the radiation source 18 may be placed at position 130e by rotating the second portion 52 about the axis 54 relative to the first portion 50. This allows the radiation source 18 to deliver radiation from the top of the patient's head (superior to inferior).

Although several possible positions for the radiation source 18 are shown as examples, it should be understood that the radiation source 18 may be placed at other positions, such as positions that are anywhere between the examples described previously.

Also, in further embodiments, instead of, or in addition to, delivering treatment or imaging radiation to the patient while the first portion 50 rotates about the axis 28, treatment or imaging radiation may be delivered to the patient while the second portion 52 rotates about the axis 54.

Figure 2B:
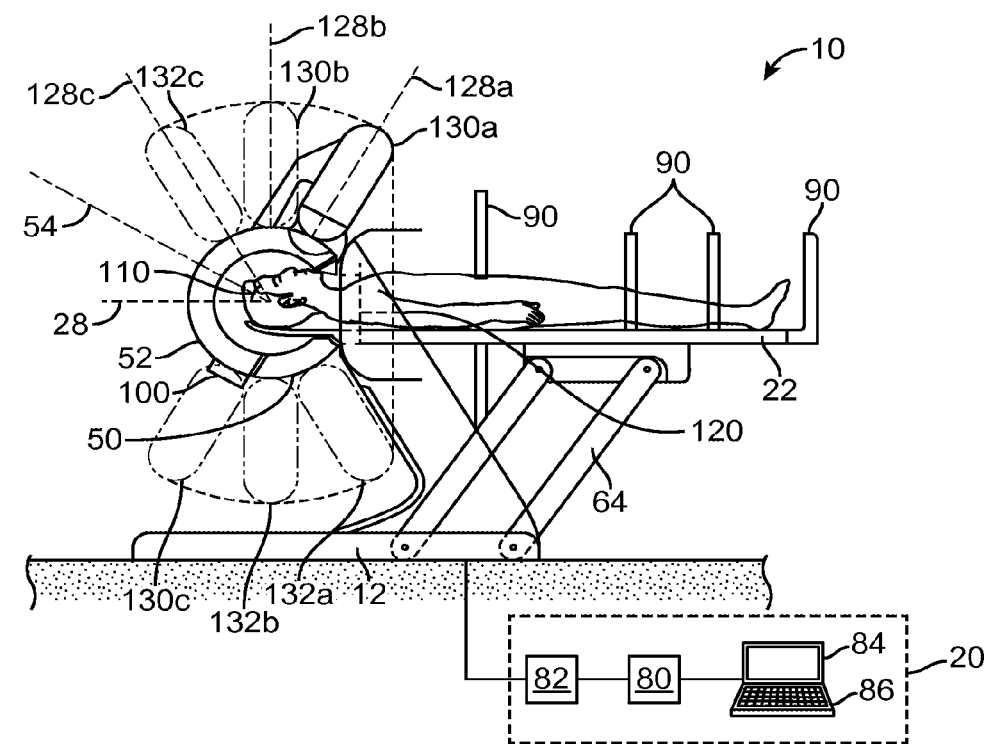
FIG. 2B illustrates another radiation system in accordance with other embodiments.

In other embodiments, the angular coverage provided by the radiation system 10 may be different from that shown in FIG. 2A by changing the relative angle 110 between the axis 28 of rotation and the axis 54 of rotation. FIG. 2B illustrates another radiation system 10 in accordance with other embodiments. The system 10 of FIG. 2B is similar to that of FIG. 2A, except that the angle 110 between the axes 28, 54 of rotation is decreased compared to that shown in FIG. 2A. Also, in the illustrated embodiments, the axis of the radiation source 18 is approximately parallel (forms a 0°±10°) to the plane of interface between the first portion 50 and the second portion 52. As a result, the possible positions achievable by the radiation source 18 is different from that shown in FIG. 2A.

In the embodiments of FIG. 2B, during use, the second portion 52 may be selectively rotated about the axis 54 relative to the first portion 50, to place the radiation source 18 at position 130a. The radiation source 18 may then be rotated around the patient by rotating the first portion 50 about the axis 28 relative to the support component 120, thereby placing the radiation source 18 at different positions around the patient (such as position 132a). As the first portion 50 is rotated about the axis 28, treatment radiation or imaging radiation may be delivered to the patient.

In another example, the second portion 52 may be selectively rotated about the axis 54 relative to the first portion 50, to place the radiation source 18 at a position that lies in plane 128b. The radiation source 18 may then be rotated around the patient by rotating the first portion 50 about the axis 28 relative to the support component 120, thereby placing the radiation source 18 at different positions around the patient (such as positions 130b, 132b). As the first portion 50 is rotated about the axis 28, treatment radiation or imaging radiation may be delivered to the patient.

In still another example, the second portion 52 may be selectively rotated about the axis 54 relative to the first portion 50, to place the radiation source 18 at position 130c. The radiation source 18 may then be rotated around the patient by rotating the first portion 50 about the axis 28 relative to the support component 120, thereby placing the radiation source 18 at different positions around the patient (such as position 132c). As the first portion 50 is rotated about the axis 28, treatment radiation or imaging radiation may be delivered to the patient.

Although several possible positions for the radiation source 18 are shown as examples, it should be understood that the radiation source 18 may be placed at other positions, such as positions that are anywhere between the examples described previously.

Also, in further embodiments, instead of, or in addition to, delivering treatment or imaging radiation to the patient while the first portion 50 rotates about the axis 28, treatment or imaging radiation may be delivered to the patient while the second portion 52 rotates about the axis 54. For example, in other embodiments, the second portion 52 may rotate relative to the first portion 50 within the plane 128a to place the radiation source 18 at different positions around the patient (such as positions 130a, 130c), while the radiation source 18 delivers treatment or imaging radiation towards the patient.

In another example, the first portion 50 may first rotate relative to the support component 120 by 180° relative to that shown in FIG. 2B. Then the second portion 52 may rotate relative to the first portion 50 within the plane 128c to place the radiation source 18 at different positions around the patient (such as positions 132a, 132c), while the radiation source 18 delivers treatment or imaging radiation towards the patient. In other examples, the first portion 50 may be rotated relative to the support component 120 by other angles (different from) 180° relative to that shown in FIG. 2B.

Figure 3A:
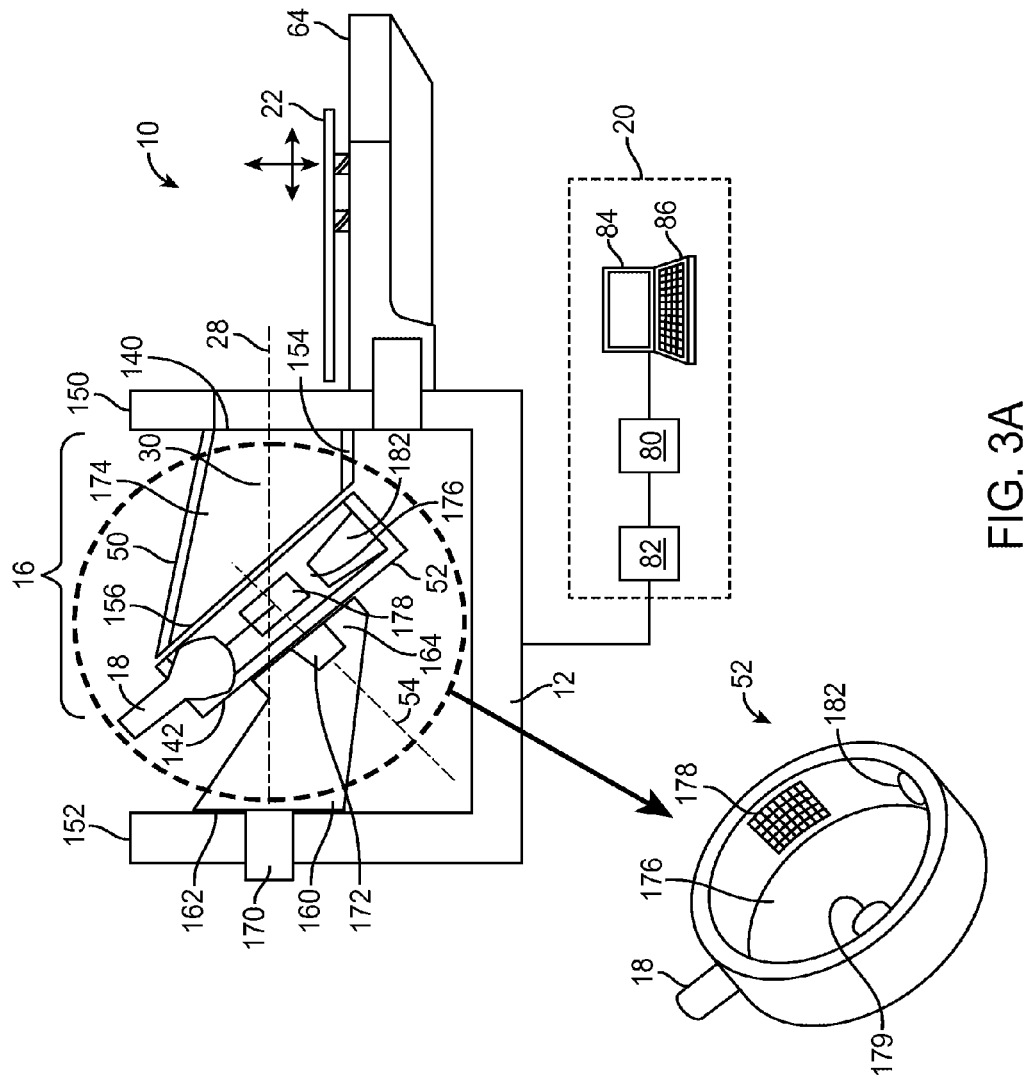
FIGS. 3A-3K illustrate another radiation system in accordance with other embodiments.

In the embodiments of FIG. 2B, the capsule 16 is supported by the support structure 14 on one side of the capsule 16. However, in other embodiments, the system 10 may further include an additional support on the opposite side of the capsule 16. FIG. 3A illustrates a variation of the system 10 of FIG. 2B in accordance with some embodiments. The degree of movement for the radiation source 18 in the system 10 of FIG. 3A is similar to that of FIG. 2B, except that the capsule 16 has a different shape, and the capsule 16 is rotatably supported at a first end 140, and a second end 142 of the capsule 16. In the illustrated embodiments, the base 12 is coupled to (e.g., integrally formed with) a first support 150 and a second support 152. The system 10 also includes a support member 160 disposed between the support 152 and the second portion 52 of the capsule 16. The support member 160 has an end 162 that is rotatably coupled to the support 152, and another end 164 that is rotatably coupled to the second portion 52 of the capsule 16. Thus, the second portion 52 is rotatably coupled between the first portion 50 and the support member 160, and the first portion 50 and the support member 160 are in turn, rotatably coupled to the supports 150, 152, respectively. The rotatably coupling between the various components may be implemented using bearings in some embodiments, such as large ring bearings. As shown in the figure, the system 10 also includes a first motor 170 for turning the support member 160 about the axis 28 relative to the support 152, and a second motor 172 for turning the second portion 52 about the axis 54 relative to the support member 160 and relative to the first portion 50.

In the illustrated embodiments, the first portion 50 defines a space 174, and the second portion 52 defines a space 176, wherein the space 174 and the space 176 together form the space 30 for accommodating a portion of a patient. The support table 22 may be positioned by positioner 64 during use, which may be configured to translate the table 22 longitudinally and/or vertically. In other embodiments, the positioner 64 may also be configured to shift the table 22 laterally left and right, and/or to rotate the table 22 in one or more degrees of freedom.

As shown in the figure, the second portion 152 also includes an imager 178 on one side of the second portion 152, and an imaging source 179 located on the opposite side of the second portion 152. Also, the second portion 152 includes the radiation source 18 attached thereto, and a beam stop 182 on the opposite side. The beam stop 182 provides shielding of the primary beam and may be made from tungsten or lead in some embodiments. The portion facing the patient is preferably concave to better shield scattered ionizing radiation. It should be noted that the beam stop 182 may be included in other embodiments described herein, even if the figures do not explicitly show it. The imaging source 179 may be a x-ray source (e.g., in keV range), a MRI component, an ultrasound source, or any component that is capable of generating energy for imaging purpose. Although the radiation source 18, the imaging source 179, and the beam stop 182 are illustrated as protruding into the space 176, in other embodiments, these components may not protrude into the space 176. During use, the imaging source 179 and the imager 178 may be used to obtain image(s) of a portion of the patient that is disposed therebetween. Such may be performed before a treatment session begins (e.g., to register the position of the patient/target region). Alternatively, the imaging may be performed during treatment session (e.g., to track and/or to verify a position of a target region).

Figure 3B:
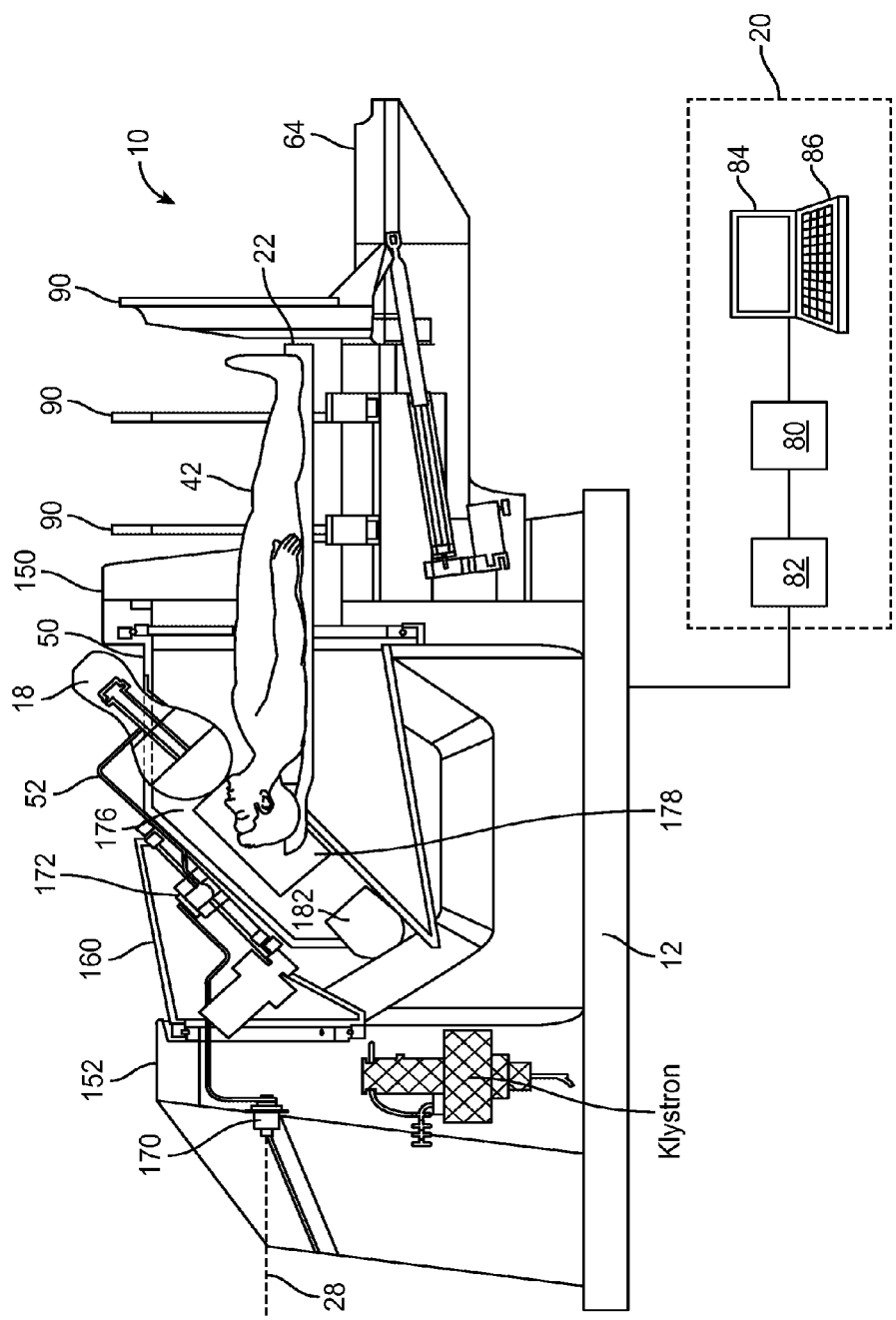

FIG. 3B illustrates an implementation of the system 10 of FIG. 3A in accordance with some embodiments, particularly showing the system 10 being used with a patient 42. During use, the patient 42 is supported on the table 22, and the positioner 64 moves the table 22 along its longitudinal axis to slide a portion of the patient 22 through an opening at the support 150, and through the space 174 of the first portion 50, so that a target area (brain tissue in the example shown) is located in the space 176 within the second portion 52. As shown in the figure, the second portion 52 may have an imager 178 on one side of the space 176, and an imaging source 179 (shown in FIG. 3A) on the opposite side of the space 176, so that a part of the patient may be imaged by the imaging source 179 and the imager 178.

As shown in the figure, the system 10 may include additional shields 90. The shield(s) 90 and the capsule 16 may cooperate to block off at least 98%, and more preferably at least 99.9%, and even more preferably at least 99.999%, of the radiation resulted from an operation of the radiation source 18. In other embodiments, the shield(s) 90 itself may block off most of the radiation resulted from an operation of the radiation source 18. In some embodiments, the shields 90 may be moveable relative to the patient support 22. For example, in some embodiments, each shield 90 may have a left portion and a right portion that are housed underneath the support 22 (e.g., on opposite sides of the positioner 64). After the patient is placed on the support 22, the left and right portions of the shield 90 from the left and right sides of the positioner 64, respectively, may then be moved up to a closed position, thereby surrounding parts of the patient.

It should be noted that any of the features related to shielding discussed with reference to the embodiments of FIG. 1 may be included in the embodiments of FIG. 3. For example, in some embodiments, the capsule 16 includes a shielding material that is configured to block at least some of the radiation that is resulted from an operation of the radiation source 18. In some embodiments, the shielding material may be used to make the wall of the capsule 16. In other embodiments, the shielding material may be coupled to the wall of the capsule 16. For examples, the shielding material may be coupled to an outside surface of the wall of the capsule 16, an inside surface of the wall of the capsule 16, or may be a layer that is embedded within the wall of the capsule 16. In addition, in other embodiments, the shielding material may be in a form of multiple layers that are coupled to the capsule 16, with one or more layers coupled to an outside surface of the wall of the capsule 16, one or more layers embedded in the wall of the capsule 16, one or more layers coupled to an inside surface of the wall of the capsule 16, or combination thereof. Also, in some embodiments, the shielding material may be configured (e.g., have certain material density, certain geometry, and/or certain thickness) to block radiation so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding.

In some embodiments, movement of the components of the system 10 of FIG. 3 (e.g., the support member 160, the first portion 50, the second portion 52, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

Figure 3C:
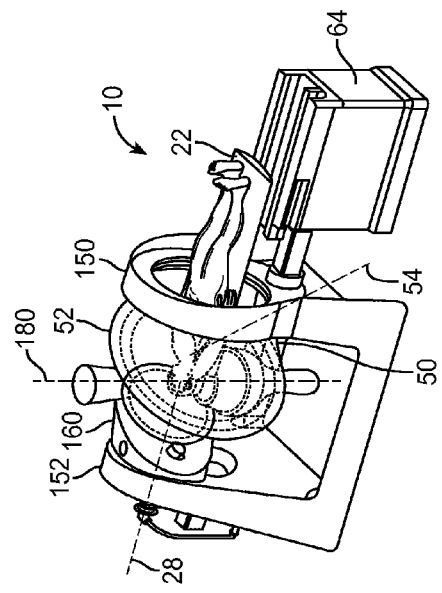

FIGS. 3C-3H illustrates some movement configurations that may be accomplished using the system 10 of FIG. 3B. As shown in FIG. 3C, the second portion 52 may be rotated relative to the first portion 50 and the support member 160 (on opposite sides of the portion 52) until the axis 180 (e.g., beam axis) of the radiation source 18 is approximately perpendicular (e.g., 90°±10°) to the axis 28 of rotation to reach the configuration shown in the figure. Then the support member 160, and the first and second portions 50, 52 of the capsule 16 may be rotated together about the axis 28 to turn the radiation source 18 about the patient. For example, after the components 50, 52, 160 have been rotated by 90°, the system 10 will have a configuration shown in FIG. 3D. In the example shown, the path of the radiation source 18 lies in a plane that is approximately perpendicular to the axis 28.

Alternatively, from the position shown in FIG. 3C, the portion 52 carrying the radiation source 18 may be rotated about the axis 54 to turn the portion 52 relative to the components 160, 50. For example, after the second portion 52 has been rotated by 90° about the axis 54, the system 10 will have a configuration shown in FIG. 3E. In the example shown, the path of the radiation source 18 relative to the support member 152 lies in a plane that forms a non-perpendicular angle relative to the axis 28.

Figure 3D:
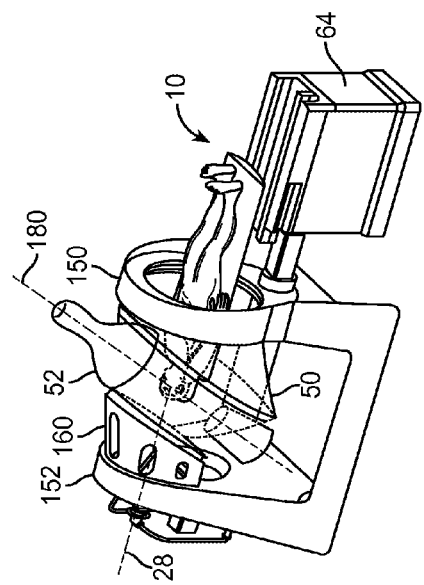
Figure 3E:
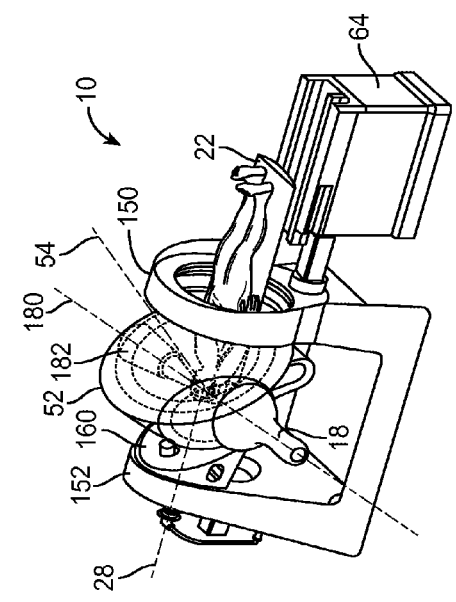
Figure 3F:
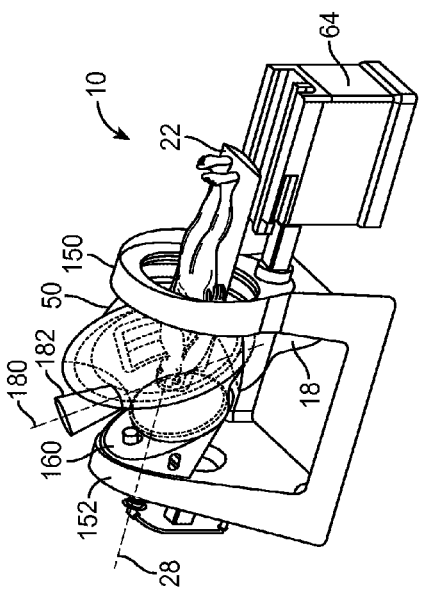

Also, in another example, from the position shown in FIG. 3E, the support member 160, and the first and second portions 50, 52, may be rotated together about the axis 28 by 180° to achieve the configuration shown in FIG. 3F.

Figure 3G:
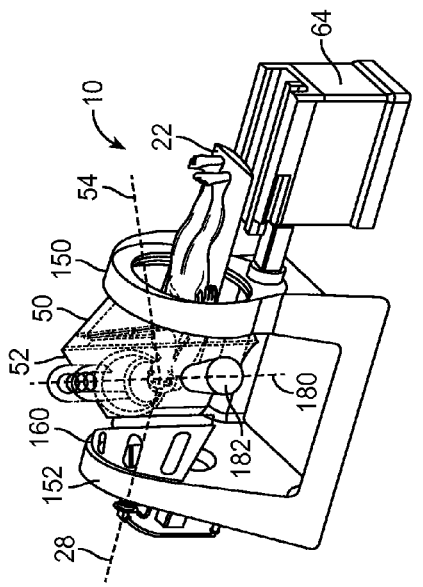

It should be noted that at any given configuration formed by the components 50, 52, 160, the second portion 52 may be rotated about the axis 54 relative to the two adjacent components 50, 160 to turn the radiation source 18 around the patient so that energy can be delivered towards the patient from various angular positions. For example, from the configuration shown in FIG. 3D, the second portion 52 may be rotated about the axis 54 relative to the components 50, 160 to turn the radiation source 18 around the patient. In such cases, the rotational path of the radiation source 18 lies in a plane that forms a non-perpendicular angle relative to the axis 28. FIG. 3G shows the configuration of the system 10 when the component 52 of FIG. 3D is rotated 90° about the axis 54.

Also, at any given configuration formed by the components 50, 52, 160, all three components 50, 52, 160 may be rotated about the axis 28 relative to the supports 150, 152 to turn the radiation source 18 around the patient so that energy can be delivered towards the patient from various angular positions. For example, from the configuration shown in FIG. 3D, the components 50, 52, 160 may be rotated about the axis 28 together to turn the radiation source 18 around the patient. In such cases, the rotational path of the radiation source 18 lies in a plane that is perpendicular to the axis 28. FIG. 3C shows the configuration of the system 10 when the components 50, 52, 160 of FIG. 3D are rotated 90° about the axis 28.

Figure 3H:
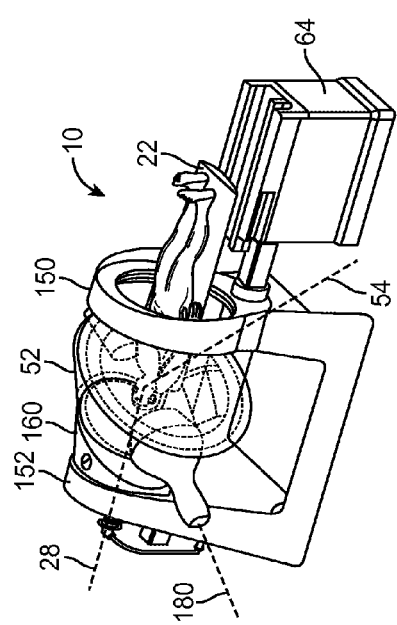

It should be noted that the possible configurations that may be achieved by the system 10 are not limited to the examples described, and that the system 10 may accomplish other configurations in other embodiments. For example, FIG. 3H shows another configuration that may be achieved by turning the support member 160, and/or the portion 52.

In one or more embodiments, the rotation of the components 50, 52, 160 about the axis 28 may be accomplished by activating the motor 170 (FIG. 3B). While the components 50, 52, 160 are being rotated about the axis 28, the second portion 52 may remain fixed in position relative to the two adjacent components 50, 160. Such may be accomplished using a locking mechanism that locks the second portion 52 in place relative to the first portion 50 and the support member 160. Alternatively, while the components 50, 52, 160 are being rotated about the axis 28, the second motor 172 may also be activated to turn the second portion 52 relative to the two adjacent components 50, 160. Activating the motors 170, 172 simultaneously is advantageous because it allows the system 10 to form a desired configuration within a shorter amount of time (compared to when the motors 170, 172 are sequentially activated), thereby reducing treatment time for the patient.

Figure 3I:
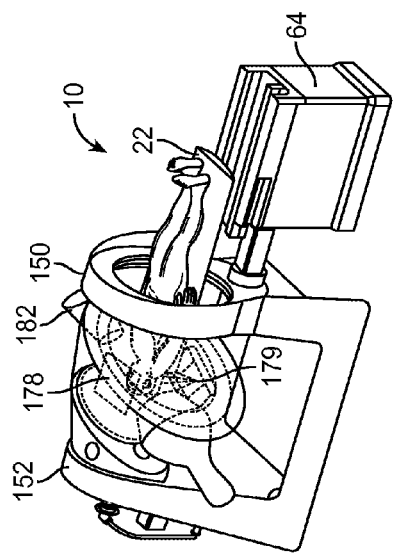

As discussed, the system 10 may include an imager 178 and a corresponding imaging source 179. FIG. 3I illustrates the system 10, particularly showing the imager 178 and the imaging source 179 in relation with the rest of the components of the system 10. Although one set of imager 178 and imaging source 179 is shown in the example, in other embodiments, the system 10 may have two sets of imagers 178 and imaging sources 179 that are placed at 90° (or at any of other angles) relative to each other.

As discussed, the system 10 may optionally include one or more shields 90. FIG. 3J illustrates the system 10 of FIG. 3B, particularly showing the system 10 having a shield 90. The shield 90 has a right portion 190 and a left portion 192. During use, the right and left portions 190, 192 of the shield 90 may be retracted below the patient support 22 and/or next to the positioner 64. After the patient has been placed on the patient support 22, the right and left portions 190, 192 of the shield 90 may be moved mechanically upward to a closed position, thereby creating an enclosure that completely surrounds the patient.

Figure 3K:
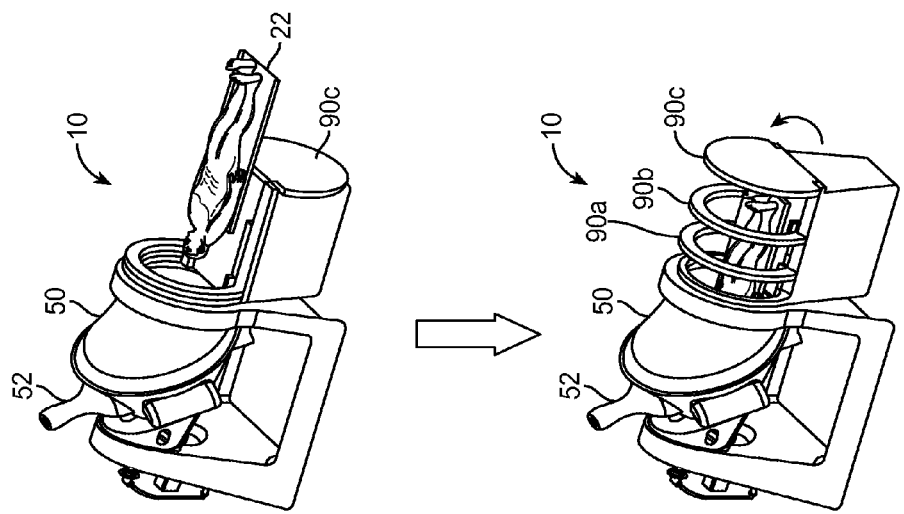
Figure 3J:
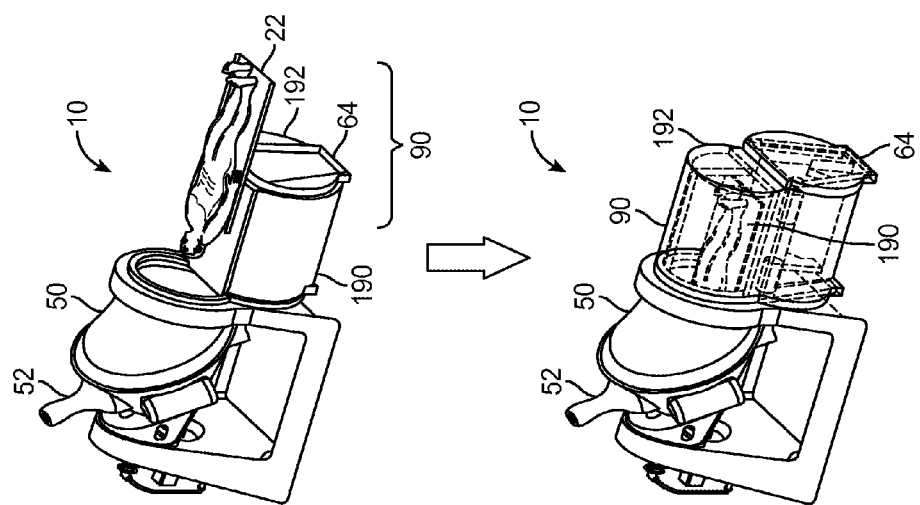

FIG. 3K illustrates another variation of the system 10, particularly showing the system having a plurality of shields 90a-90c. Each of the shields 90a, 90b has a left portion and a right portion, which may be retracted below the patient support 22 and/or next to the positioner 64. After the patient has been placed on the patient support 22, the left and right portions of each of the shields 90a, 90b may be moved mechanically upward to a closed position. Also, the shield 90c may be placed at an open position below the patient support 22. After the patient has been placed on the patient support 22, the shield 90c may be rotated about a hinge to swing the shield 90c to a closed position. The shields 90a-90c collectively function to block (attenuate) radiation emitting out of the capsule 16 that is resulted from the operation of the radiation source 18, while allowing parts of the patient to be visible from outside the system 10. In some embodiments, a shielding wall (e.g., lead glass) may be coupled between the shields 90a, 90b to further attenuate radiation.

Figure 4:
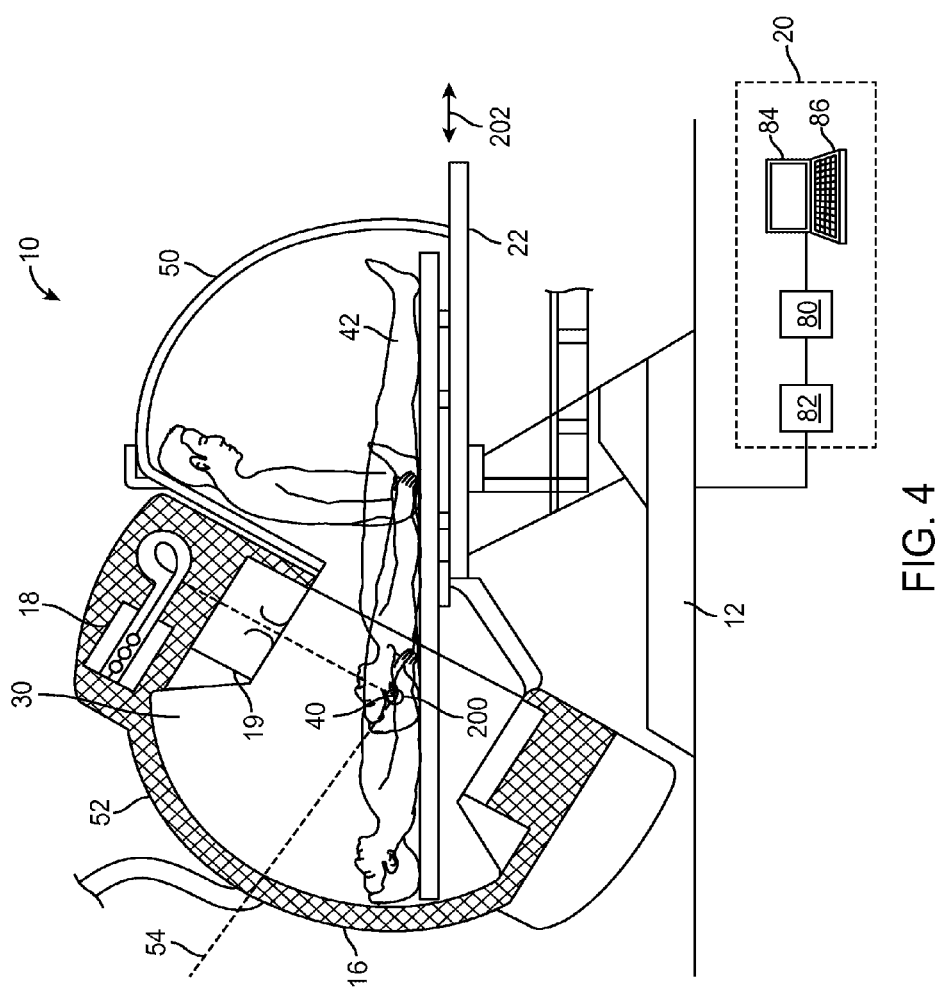
FIG. 4 illustrates another radiation system in accordance with other embodiments.

FIG. 4 illustrates another radiation system 10 in accordance with other embodiments. The radiation system 10 of FIG. 4 is similar to the system 10 of FIG. 1, except that the capsule 16 has a different configuration. As shown in the figure, the capsule 16 has a size that surrounds the patient 42. The capsule 16 has a first portion 50, and a second portion 52 that rotates relative to the first portion 50 about axis 54. The second portion 52 of the capsule 16 carries the radiation source 18, which is configured to deliver treatment radiation and/or diagnostic radiation. During use, the second portion 52 of the capsule 16 rotates about the axis 54 to thereby place the radiation source 18 at different gantry position with respect to the portion 40 of the patient 42 that is desired to be treated and/or imaged. The radiation source 18 may be the same radiation source 18 as that discussed with reference to FIG. 1. In the illustrated embodiments, the SID/SAD is less than 800 mm, and more preferably less than 600 mm, and even more preferably about 415 mm (415 mm±40 mm). Also, in some embodiments, the SID/SAD value for the radiation system 10 is less than those in existing radiation machines. In other embodiments, the SID/SAD may have other values (e.g., a value that is larger than 600 mm).

In some embodiments, the capsule 16 may optionally be configured to also rotate about an axis that is perpendicular to the axis 54. For example, in some embodiments, the capsule 16 may also be configured to rotate about an axis that coincides with an isocenter 200 of the system 10, and that extends perpendicular to the axis 54 out of the page of the figure. The support 22 may be configured to translate the patient 42 (e.g., in the directions represented by the arrows 202) to thereby place different parts of the patient 42 at the isocenter 200.

It should be noted that any of the features related to shielding discussed with reference to the embodiments of FIG. 1 may be included in the embodiments of FIG. 4. For example, in some embodiments, the capsule 16 includes a shielding material that is configured to block at least some of the radiation that is resulted from an operation of the radiation source 18. In some embodiments, the shielding material may be used to make the wall of the capsule 16. In other embodiments, the shielding material may be coupled to the wall of the capsule 16. For examples, the shielding material may be coupled to an outside surface of the wall of the capsule 16, an inside surface of the wall of the capsule 16, or may be a layer that is embedded within the wall of the capsule 16. In addition, in other embodiments, the shielding material may be in a form of multiple layers that are coupled to the capsule 16, with one or more layers coupled to an outside surface of the wall of the capsule 16, one or more layers embedded in the wall of the capsule 16, one or more layers coupled to an inside surface of the wall of the capsule 16, or combination thereof. Also, in some embodiments, the shielding material may be configured (e.g., have certain material density, certain geometry, and/or certain thickness) to block radiation so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding.

Also, in further embodiments, the system 10 of FIG. 4 may optionally include one or more shields 90, as similarly discussed. The shield(s) 90 and the capsule 16 may cooperate to block off at least 98%, and preferably at least 99.9%, and even more preferably at least 99.999%, of the radiation resulted from an operation of the radiation source 18. In some embodiments. In other embodiments, the shield(s) 90 itself may block off most of the radiation resulted from an operation of the radiation source 18.

In some embodiments, movement of the components of the system 10 of FIG. 4 (e.g., the capsule 16, the portion 52, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

Figure 5:
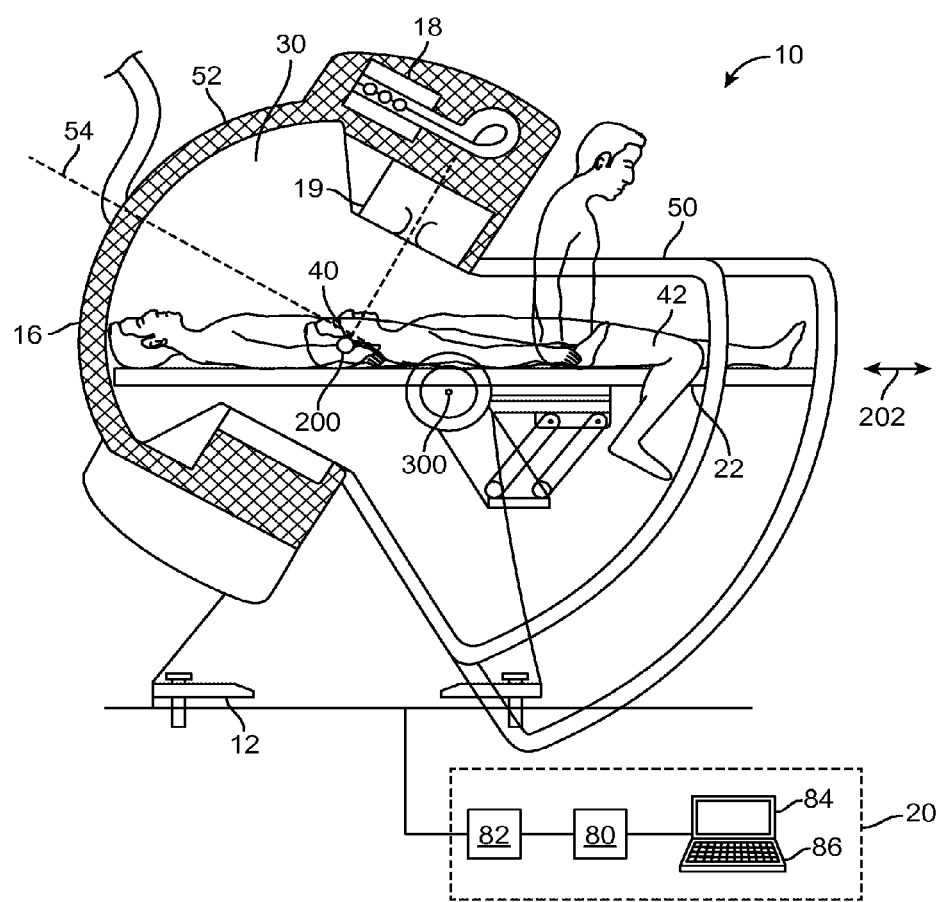
FIG. 5 illustrates another radiation system in accordance with other embodiments.

FIG. 5 illustrates another radiation system 10 in accordance with other embodiments. The radiation system 10 of FIG. 5 is similar to the system 10 of FIG. 4, except that the capsule 16 has a different configuration. As shown in the figure, the capsule 16 provides a complete enclosure that surrounds the entire patient 42 and the support 22. The capsule 16 has a first portion 50, and a second portion 52 that rotates relative to the first portion 50 about axis 54. Part of the capsule 16 may be a door that is moveably coupled to the rest of the capsule 16 to thereby allow the patient 42 to enter into and exit out of the capsule 16. The second portion 52 of the capsule 16 carries the radiation source 18, which is configured to deliver treatment radiation and/or diagnostic radiation. During use, the second portion 52 of the capsule 16 rotates about the axis 54 to thereby place the radiation source 18 at different gantry position with respect to the portion 40 of the patient 42 that is desired to be treated and/or imaged. The radiation source 18 may be the same radiation source 18 as that discussed with reference to FIG. 1. In the illustrated embodiments, the SID/SAD is less than 800 mm, and more preferably less than 600 mm, and even more preferably about 415 mm (415 mm±40 mm). Also, in some embodiments, the SID/SAD value for the radiation system 10 is less than those in existing radiation machines. In other embodiments, the SID/SAD may have other values (e.g., a value that is larger than 600 mm).

In some embodiments, the capsule 16 may optionally be configured to also rotate about an axis that is perpendicular to the axis 54. For example, in some embodiments, the capsule 16 may also be configured to rotate about an axis that coincides with an isocenter 200 of the system 10, and that extends perpendicular to the axis 54 out of the page of the figure. In another example, the capsule 16 may be configured to rotate about axis 300, which is offset from the isocenter 200, and extends out of the page of the figure in a direction that is perpendicular to the axis 54. In some embodiments, the patient support 22 inside the capsule 16 may be coupled to the structural support 12 outside the capsule 16 through a shaft/hinge that extends through the wall of the capsule 16 that connects to the support 12. Such configuration allows the patient support 22 to remain rotationally fixed relative to the support 12 as the capsule 16 is rotated about the axis through the isocenter 200 or the axis 300. Such configuration also allows the capsule 16 to rotate relative to the patient support 22 without carrying the patient support 22 with it as it rotates. The support 22 may be configured to translate the patient 42 (e.g., in the directions represented by the arrows 202) to thereby place different parts of the patient 42 at the isocenter 200. The support 22 may also be configured to move in different degrees of freedom, such as those described with reference to the embodiments of FIG. 1.

It should be noted that any of the features related to shielding discussed with reference to the embodiments of FIG. 1 may be included in the embodiments of FIG. 5. For example, in some embodiments, the capsule 16 includes a shielding material that is configured to block at least some of the radiation that is resulted from an operation of the radiation source 18. In some embodiments, the shielding material may be used to make the wall of the capsule 16. In other embodiments, the shielding material may be coupled to the wall of the capsule 16. For examples, the shielding material may be coupled to an outside surface of the wall of the capsule 16, an inside surface of the wall of the capsule 16, or may be a layer that is embedded within the wall of the capsule 16. In addition, in other embodiments, the shielding material may be in a form of multiple layers that are coupled to the capsule 16, with one or more layers coupled to an outside surface of the wall of the capsule 16, one or more layers embedded in the wall of the capsule 16, one or more layers coupled to an inside surface of the wall of the capsule 16, or combination thereof. Also, in some embodiments, the shielding material may be configured (e.g., have certain material density, certain geometry, and/or certain thickness) to block radiation so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding.

Also, in further embodiments, the system 10 of FIG. 5 may optionally include one or more shields 90, as similarly discussed. The shield(s) 90 and the capsule 16 may cooperate to block off at least 98%, and preferably at least 99.9%, and even more preferably at least 99.999%, of the radiation resulted from an operation of the radiation source 18. In some embodiments. In other embodiments, the shield(s) 90 itself may block off most of the radiation resulted from an operation of the radiation source 18.

In some embodiments, movement of the components of the system 10 of FIG. 5 (e.g., the capsule 16, the portion 52, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

Figure 6:
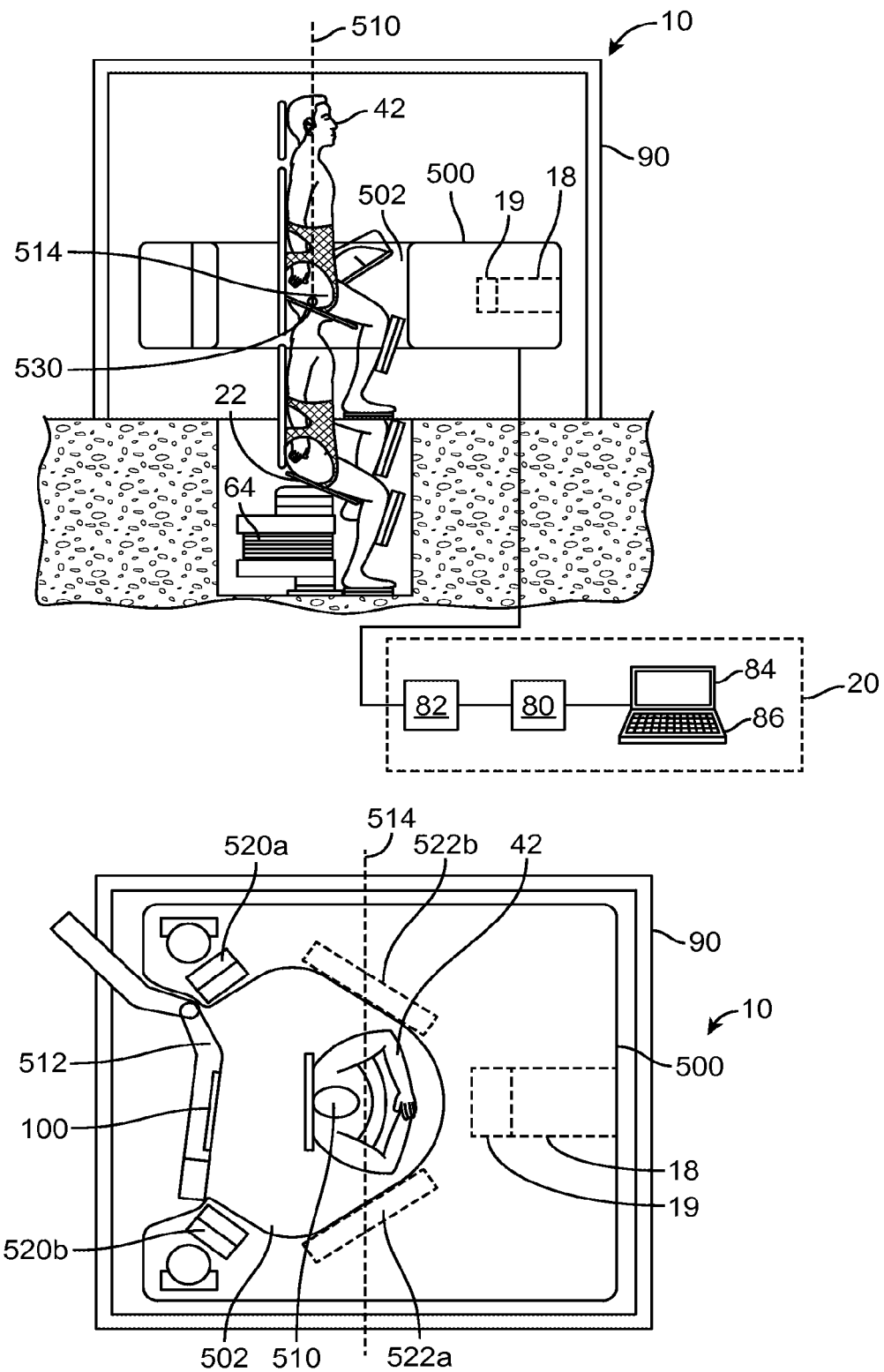
FIG. 6 illustrates another radiation system in accordance with other embodiments.

FIG. 6 illustrates another radiation system 10 in accordance with other embodiments. The system 10 includes a patient support 22, a gantry 500, a radiation source 18 coupled to the gantry 500, and a collimator 19 for configuring radiation (e.g., changing a shape of the radiation beam) provided by the radiation source 18. In the illustrated embodiments, the patient support 22 is configured to support the patient 42 in an upright position. In one implementation, the patient support 22 may be implemented as a medical chair. The patient support 22 is also configured to rotate by a positioner 64 about an axis 510 during use, so that the patient 42 may be rotated relative to the radiation source 18. Because the patient 42 is rotated by the patient support 22, the gantry 500 carrying the radiation source 18 does not need to be rotated. Instead, the gantry 500 is configured to move vertically in an upward or downward position so that the radiation source 18 may deliver radiation to different part(s) of the patient 42. In such cases, the gantry 500 may be slidably coupled to a vertical rail, for example.

In other embodiments, the positioner 64 may also be configured to move the patient support 22 vertically upward or downward. In such cases, the gantry 500 is not required to move vertically (e.g., the gantry 500 may be fixedly mounted to a structure, such as a component of the system 10, a part of a room, etc.). However, in some embodiments, the gantry 500 may optionally be configured to move vertically anyway. In further embodiments, the gantry 500 may optionally be configured to tilt relative to the patient 42. For example, in some embodiments, the gantry 500 may be configured to rotate about an axis 514, so that the radiation source 18 may deliver radiation towards the patient 42 at different angular positions.

As shown in the figure, the gantry 500 includes a door 512 for allowing the patient 42 to enter into the space 502 surrounded by the gantry 500. The door 512 may optionally include an imager 100, so that when the door 512 is closed, the imager 100 is at an operative position relative to the radiation source 18. During use, radiation from the radiation source 18 enters the patient 42 and exits the patient 42 to reach the imager 100. The imager 100 generates image data in response to the radiation received thereon. The radiation may be treatment radiation in some embodiments, or diagnostic radiation in other embodiments. In some embodiments, the image data may be generated before a treatment session using diagnostic radiation to setup the patient 42 (e.g., before treatment radiation is delivered to the patient 42). In other embodiments, the image data may be generated during a treatment session to confirm an accuracy of treatment radiation delivery. In further embodiments, the image data may be processed by the processor 80, which adjusts a treatment plan based on the processed image data. For example, if the processor 80 determines from the image data that a part of a target region is not receiving enough radiation, and/or if a critical (e.g., healthy) tissue is receiving too much radiation, the processor 80 may then adjust the treatment plan so that a future delivery of treatment radiation would result in more radiation being delivered to the target region and/or less radiation being delivered to the critical tissue.

The radiation source 18 may be the same radiation source 18 as that discussed with reference to FIG. 1. In the illustrated embodiments, the SID/SAD is less than 800 mm, and more preferably less than 600 mm, and even more preferably about 415 mm (415 mm±40 mm). Also, in some embodiments, the SID/SAD value for the radiation system 10 is less than those in existing radiation machines. Such configuration allows the radiation source 18 to provide less radiation energy compared to existing treatment radiation sources, and still sufficiently treats a target (e.g., tumor). Also, because of the reduction in energy requirement, the amount of shielding that is needed for a facility building is substantially reduced, or may be eliminated. In other embodiments, the SID/SAD may have other values (e.g., a value that is larger than 600 mm).

In the illustrated embodiments, the radiation system 10 also includes a shield 90 surrounding the gantry 500. The shield 90 is configured to block at least some of the radiation that is resulted from an operation of the radiation source 18. In some embodiments, the shield 90 may be configured (e.g., have certain material density, certain geometry, and/or certain thickness) to block radiation so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shield 90 may be configured to block off a sufficient amount of radiation resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shield 90 may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding.

In some embodiments, movement of the components of the system 10 of FIG. 6 (e.g., the support 22, the source 18, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

As shown in the figure, the radiation system 10 may optionally further include two imaging sources 520*a*, 520*b* (e.g., two x-ray sources) and two corresponding imagers 522*a*, 522*b* that are in corresponding operative positions relative to the imaging sources 520*a*, 520*b*. In other embodiments, the imaging sources 520*a*, 520*b* and the imagers 522*a*, 522*b* may be coupled to another structure that is not a part of the radiation system 10. For example, in other embodiments, the imaging sources 520*a*, 520*b* and the imagers 522*a*, 522*b* may be mounted to a room (e.g., to a ceiling, a floor), or to a support that is movable independent of the gantry 500. During use, radiation from the imaging sources 520*a*, 520*b* enters the patient 42 and exits the patient 42 to reach the corresponding imagers 522*a*, 522*b*. The imagers 522*a*, 522*b* generate image data in response to the radiation received thereon. In some embodiments, the image data may be generated before a treatment session using diagnostic radiation to setup the patient 42 (e.g., before treatment radiation is delivered to the patient 42). In other embodiments, the image data may be generated during a treatment session to confirm an accuracy of treatment radiation delivery. In further embodiments, the image data may be processed by the processor 80, which adjusts a treatment plan based on the processed image data. For example, if the processor 80 determines from the image data that a part of a target region is not receiving enough radiation, and/or if a critical (e.g., healthy) tissue is receiving too much radiation, the processor 80 may then adjust the treatment plan so that a future delivery of treatment radiation would result in more radiation being delivered to the target region and/or less radiation being delivered to the critical tissue.

In other embodiments, the radiation system 10 may not include both imaging sources 520*a*, 520*b* and both imagers 522*a*, 522*b*. Instead, the radiation system 10 may include only one imaging source, and one corresponding imager. In further embodiments, the radiation system 10 may not include any imaging source and imager.

In one or more embodiments described herein (e.g., in the embodiments of FIG. 1, FIGS. 2A-2B, FIG. 3, FIG. 4, FIG. 5, or FIG. 6), the system 10 may have a light weight and/or weight distribution. For example, in some embodiments, the system 10 may have a total weight that is less than 20 k lbs, and more preferably, less than 15 k lbs (e.g., 10 k lbs). Alternatively or additionally, in some embodiments, the system 10 may have a weight per square feet that is less than 500 lb/ft$^2$, and more preferably, less than 400 lb/ft$^2$, such as 300 lb/ft$^2$ or less (e.g., 200 lb/ft$^2$). Configuring the system 10 to have a light weight and/or weight distribution is advantageous because it may obviate the need to retrofit a building in order to support the system 10. Also, such configuration may allow the system 10 to be placed in other floors that are higher than the basement. Various techniques may be employed to reduce a weight and/or a weight distribution of the system 10. For example, in some embodiments, a light weight accelerator (e.g., a X-band accelerator) may be used for the system 10. In one implementation, an energy requirement of the accelerator may be reduced by reducing the SID/SAD (e.g., to 800 mm or less), thereby reducing a required dose-rate output of the accelerator. This may in turn, reduce a size of the accelerator in some embodiments. Also, in some embodiments, light weight materials may be used to make different components of the radiation system 10. In further embodiments, a desired weight distribution of the system 10 may be achieved by distributing one or more components of the system 10 over a larger surface area. For example, in some embodiments, the shielding material (e.g., the shielding material at the capsule 16 and/or at the shield(s) 90) for the radiation system 10 may be implemented using different shielding portions that are placed at different distances away from a part of the system 10. In one implementation, there may be a first shielding portion that is located closer to an isocenter of the system 10, and a second shielding portion that is located further away from the isocenter than the first shielding portion. In such cases, during a radiation procedure, radiation generated may be partially blocked by the first shielding portion, and then further blocked by the second shielding portion. Thus, in some embodiments, a radiation shielding for the system 10 may be implemented using different shielding portions (which may be considered to be parts of the capsule 16 and/or the shield 90). As long as these shielding portions are not retrofitted into the structures of a building, they may be considered to be parts of the system 10. In some embodiments, these shielding portions may be physically coupled (directly or indirectly) to components of the system 10. In other embodiments, one or more of these shielding portions may be stand alone components that are not physically coupled to components of the system 10. Also, in some embodiments, all of the shielding for the system 10 may be located within 5 meters, and more preferably, within 3 meters, from an isocenter of the system 10.

In one or more embodiments (e.g., any of the embodiments of FIGS. 1-6), the shielding of the system 10 may be configured to achieve non-occupational exposure levels of 2 mR/hr or less in nearby uncontrolled areas of a facility (such as, within 10 meters from the system 10, and more preferably within 5 meters from the system 10, and more preferably within 3 meters from the system 10, and even more preferably within a distance of 1.5 m from the system 10—e.g., measured from an isocenter or from any surface of the system 10). Additionally, or alternatively, the shielding of the system 10 may be configured to achieve occupational exposure levels of 5 mR/hr or less are preferably achieved at the control console in the treatment room (such as, within 10 meters from the system 10, and more preferably within 5 meters from the system 10, and more preferably within 3 meters from the system 10, and even more preferably within a distance of 1.5 m from the system 10—e.g., measured from an isocenter or from any surface of the system 10). Additionally, or alternatively, in one or more embodiments (e.g., any of the embodiments of FIGS. 1-6), the shielding of the system 10 may be configured to satisfy the requirements under 10 CFR § 20.1301, which prescribes dose limits for individual members of the public. For example, in some embodiments, the shielding for the system 10 may be configured so that (1) the total effective dose equivalent to individual members of the public does not exceed 0.1 rem (1 mSv) in a year, and (2) the dose in any unrestricted area from external sources does not exceed 0.002 rem (0.02 millisievert) in any one hour.

Figure 7:
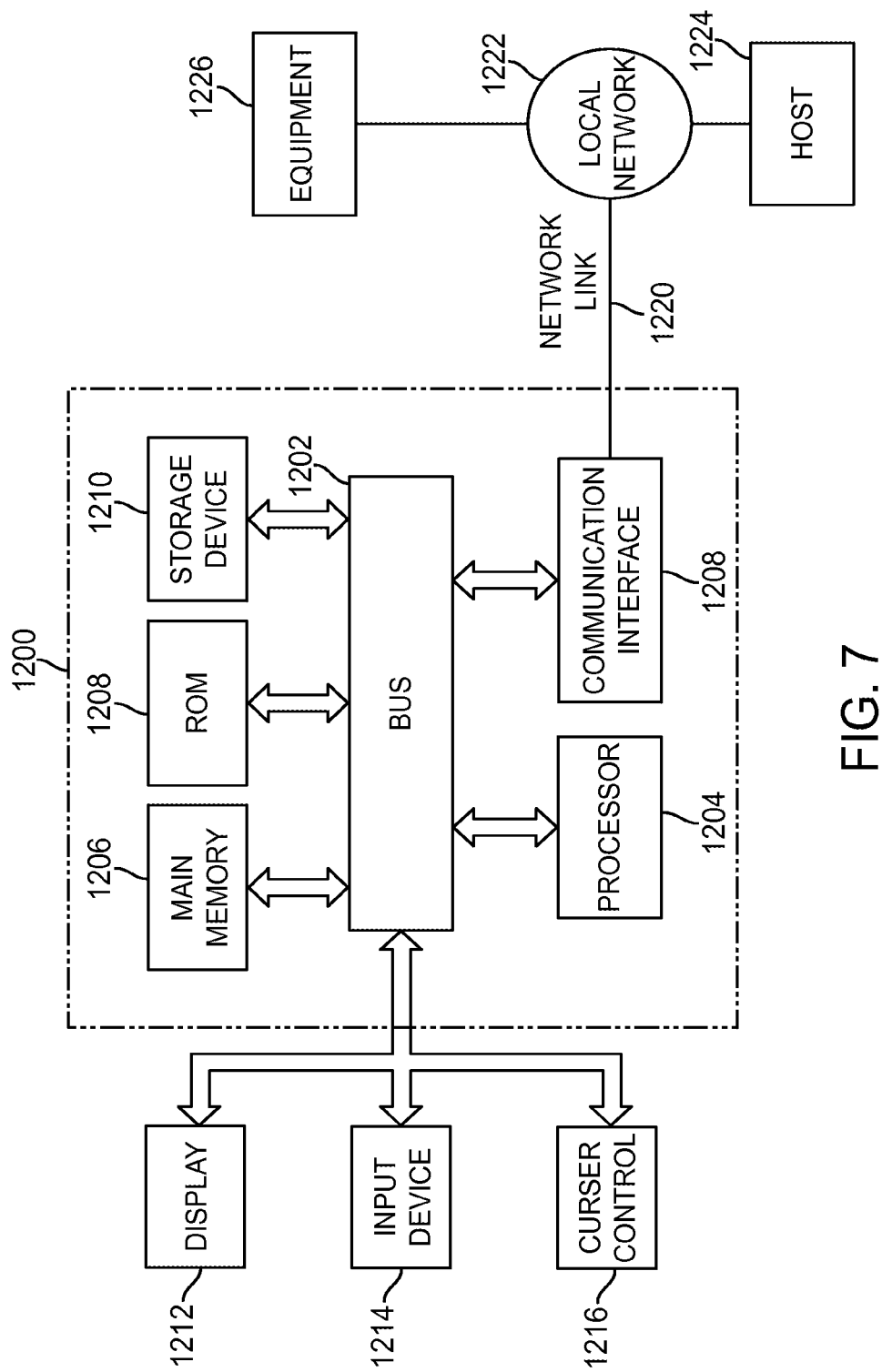
FIG. 7 illustrates an example of a computer system that may be used to implement a part of a radiation system in accordance with some embodiments.

FIG. 7 is a block diagram that illustrates an embodiment of a computer system 1200 upon which one or more components of the radiation system 10 may be implemented. In some embodiments, the computer system 1200 may be used to implement the processor 80. Computer system 1200 includes a bus 1202 or other communication mechanism for communicating information, and a processor 1204 coupled with the bus 1202 for processing information. The processor 1204 may be configured to perform various functions described herein. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT) or a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein.

One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the processor described herein are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media (an example of non-transitory media) includes, for example, optical or magnetic disks, such as the storage device 1210. Volatile media (another example of non-transitory media) includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network(s), the network link 1220, and the communication interface 1218.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed:

1. A radiation system, comprising:
   a first support;
   a second support;
   a first structure rotatably coupled to the first support;
   a second structure carrying a radiation outlet, wherein the radiation outlet is configured to emit a treatment radiation beam; and
   a third structure rotatably coupled to the second support;
   wherein the second structure is located between the first structure and the third structure, and is rotatably coupled to the first structure and the third structure;
   wherein the first structure is rotatable about a first axis, and the second structure is rotatable about a second axis that is different from the first axis; and
   wherein the first structure, the second structure, and the third structure are respective mechanical components of the radiation system that is configured to provide the treatment radiation beam.

2. The system of claim 1, wherein the second structure is a part of a capsule for accommodating a portion of a patient.

3. The system of claim 1, wherein the second structure includes a shielding material configured to limit a radiation exposure level to 5 m R/hr or less within 5 meters from an isocenter.

4. The system of claim 1, wherein the radiation outlet is coupled to a linear accelerator.

5. The system of claim 1, wherein the radiation outlet is configured to emit radiation having an energy range that is anywhere between 0.2 MV to 8 MV.

6. The system of claim 1, further comprising a patient support for supporting a patient.

7. The system of claim 6, wherein the first structure comprises an opening, and the patient support is configured to translate the patient to insert a portion of the patient into the first structure through the opening.

8. The system of claim 6, further comprising a base, wherein the first support, the second support, and the patient support are coupled to the base to thereby allow the system as a whole to be transported in one unit.

9. The system of claim 1, wherein the first structure is rotatable about a first axis that is approximately horizontal.

10. The system of claim 1, further comprising an imager located at an operative position relative to the radiation outlet.

11. The system of claim 1, further comprising one or more diagnostic radiation sources, and one or more imagers that correspond with the respective one or more diagnostic radiation sources.

12. The system of claim 1, wherein the system has a total weight that is less than 20k lbs.

* * * * *